(12) United States Patent
Natan

(10) Patent No.: US 9,297,766 B2
(45) Date of Patent: *Mar. 29, 2016

(54) METHOD OF TAGGING MATERIALS WITH SURFACE-ENHANCED SPECTROSCOPY-ACTIVE SANDWICH PARTICLES

(75) Inventor: Michael J. Natan, San Carlos, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 1225 days.

This patent is subject to a terminal disclaimer.

(21) Appl. No.: 11/133,926

(22) Filed: May 20, 2005

(65) Prior Publication Data

US 2005/0208665 A1 Sep. 22, 2005

Related U.S. Application Data

(63) Continuation of application No. 11/051,222, filed on Feb. 4, 2005, now abandoned, which is a continuation of application No. 10/056,808, filed on Jan. 25, 2002, now Pat. No. 6,861,263.

(60) Provisional application No. 60/264,497, filed on Jan. 26, 2001, provisional application No. 60/297,097, filed on Jun. 8, 2001.

(51) Int. Cl.
G01N 37/00 (2006.01)
G01N 21/65 (2006.01)
G01J 3/44 (2006.01)

(52) U.S. Cl.
CPC ............. *G01N 21/658* (2013.01); *G01J 3/44* (2013.01); *Y10T 436/10* (2015.01); *Y10T 436/13* (2015.01)

(58) Field of Classification Search
CPC ...... B82Y 30/00; B82Y 20/00; Y10S 977/70; Y10T 428/2918; Y10T 428/24058; Y10T 428/292; Y10T 428/30; Y10T 436/10; Y10T 436/117497; Y10T 436/118339; Y10T 436/143333; Y10T 436/14; Y10T 436/145555
See application file for complete search history.

(56) References Cited

U.S. PATENT DOCUMENTS 3,975,084 A 8/1976 Block
4,039,297 A 8/1977 Takenaka
(Continued)

FOREIGN PATENT DOCUMENTS

EP 0 653 625 5/1995
EP 0 703 454 3/1996
(Continued)

OTHER PUBLICATIONS

Tian et al. "SERS From Transition Metals and Excited by Ultraviolet Light" in "Surface-Enhanced Raman Scattering—Physics and Applications", Topics Appl. Phys., 2006, vol. 103, pp. 125-146.*
(Continued)

*Primary Examiner* — Yelena G Gakh
(74) *Attorney, Agent, or Firm* — Lerner, David, Littenberg, Krumholz & Mentlik, LLP

(57) ABSTRACT

Surface-enhanced Raman spectroscopy (SERS) uses nanoscale metal particles (SERS-active particles) or surface roughness to enhance the Raman signal of Raman-active analytes contacting the surface. SERS sandwich particles contain SERS-active particles sandwiching a Raman-active substance and serve as optical tags. Preferably, the particles are rod-shaped, with each layer (SERS-active and Raman-active) formed as a distinct stripe of the particle. These freestanding particles can be derivatized with surface ligands capable of associating with analytes of interest in, for example, a biological sample. The acquired Raman spectrum of the particle encodes the identity of the ligand. Because of the simplicity and intensity of Raman spectra, highly multiplexed assays are capable using SERS particles with different Raman-active species.

24 Claims, 2 Drawing Sheets

(56) References Cited

U.S. PATENT DOCUMENTS

| | | |
|---|---|---|
| 4,313,734 A | 2/1982 | Leuvering |
| 4,802,761 A | 2/1989 | Bowen et al. |
| 4,853,335 A | 8/1989 | Olsen et al. |
| 4,920,059 A | 4/1990 | Moeremans et al. |
| 5,023,139 A | 6/1991 | Birnboim et al. |
| 5,059,394 A | 10/1991 | Phillips et al. |
| 5,096,809 A | 3/1992 | Chen et al. |
| 5,112,127 A | 5/1992 | Carrabba et al. |
| 5,137,827 A | 8/1992 | Mroczkowski et al. |
| 5,255,067 A | 10/1993 | Carrabba et al. |
| 5,266,498 A | 11/1993 | Tarcha et al. |
| 5,384,265 A | 1/1995 | Kidwell et al. |
| 5,441,894 A | 8/1995 | Coleman et al. |
| 5,445,972 A | 8/1995 | Tarcha et al. |
| 5,552,086 A | 9/1996 | Siiman et al. |
| 5,567,628 A | 10/1996 | Tarcha et al. |
| 5,580,492 A | 12/1996 | Bonnemann et al. |
| 5,609,907 A | 3/1997 | Natan |
| 5,637,508 A | 6/1997 | Kidwell et al. |
| 5,825,790 A | 6/1997 | Lawandy |
| 5,674,699 A | 10/1997 | Saunders et al. |
| 5,786,219 A * | 7/1998 | Zhang et al. ............... 436/523 |
| 5,828,450 A | 10/1998 | Dou et al. |
| 5,833,924 A | 11/1998 | McClintock et al. |
| 5,864,397 A | 1/1999 | Vo-Dinh |
| 5,891,738 A | 4/1999 | Soini et al. |
| 5,935,755 A | 8/1999 | Kazmaier et al. |
| 5,958,704 A | 9/1999 | Starzl et al. |
| 6,020,207 A | 2/2000 | Liu |
| 6,027,890 A | 2/2000 | Ness et al. |
| 6,103,868 A | 8/2000 | Heath et al. |
| 6,136,610 A | 10/2000 | Polito et al. |
| 6,149,868 A | 11/2000 | Natan et al. |
| 6,180,415 B1 | 1/2001 | Schultz et al. |
| 6,200,820 B1 | 3/2001 | Hansen et al. |
| 6,219,137 B1 | 4/2001 | Vo-Dinh |
| 6,221,673 B1 | 4/2001 | Snow et al. |
| 6,235,241 B1 | 5/2001 | Catt et al. |
| 6,274,323 B1 | 8/2001 | Bruchez et al. |
| 6,344,272 B1 | 2/2002 | Oldenburg et al. |
| 6,361,944 B1 | 3/2002 | Mirkin et al. |
| 6,422,998 B1 | 7/2002 | Vo-Dinh et al. |
| 6,436,651 B1 | 8/2002 | Everhart et al. |
| 6,451,619 B1 | 9/2002 | Catt et al. |
| 6,500,622 B2 | 12/2002 | Bruchez, Jr. et al. |
| 6,514,767 B1 | 2/2003 | Natan |
| 6,514,770 B1 | 2/2003 | Sorin |
| 6,558,956 B1 | 5/2003 | Carron et al. |
| 6,562,403 B2 | 5/2003 | Klabunde et al. |
| 6,587,197 B1 | 7/2003 | Rahbar-Dehghan |
| 6,595,427 B1 | 7/2003 | Soni et al. |
| 6,603,537 B1 | 8/2003 | Dietz et al. |
| 6,610,351 B2 | 8/2003 | Shchegolikhin et al. |
| 6,630,307 B2 | 10/2003 | Bruchez et al. |
| 6,642,012 B1 | 11/2003 | Ashdown |
| 6,646,738 B2 | 11/2003 | Roe |
| 6,649,138 B2 | 11/2003 | Adams et al. |
| 6,653,080 B2 | 11/2003 | Bruchez et al. |
| 6,682,596 B2 | 1/2004 | Zehnder et al. |
| 6,687,395 B1 | 2/2004 | Dietz et al. |
| 6,699,724 B1 | 3/2004 | West et al. |
| 6,730,400 B1 | 5/2004 | Komatsu et al. |
| 6,743,581 B1 | 6/2004 | Vo-Dinh |
| 6,750,016 B2 | 6/2004 | Mirkin et al. |
| 6,750,031 B1 | 6/2004 | Ligler et al. |
| 6,759,235 B2 | 7/2004 | Empedocles et al. |
| 6,778,316 B2 | 8/2004 | Halas et al. |
| 6,815,064 B2 | 11/2004 | Treadway et al. |
| 6,815,212 B2 | 11/2004 | Ness et al. |
| 6,838,243 B2 | 1/2005 | Lai et al. |
| 6,861,263 B2 | 3/2005 | Natan |
| 6,919,009 B2 | 7/2005 | Stonas et al. |
| 6,970,246 B2 | 11/2005 | Hansen |
| 6,972,173 B2 | 12/2005 | Su et al. |
| 7,045,049 B1 | 5/2006 | Natan et al. |
| 7,079,241 B2 | 7/2006 | Empedocles et al. |
| 7,098,041 B2 | 8/2006 | Kaylor et al. |
| 7,102,747 B2 | 9/2006 | Wang et al. |
| 7,102,752 B2 | 9/2006 | Kaylor et al. |
| 7,105,310 B1 | 9/2006 | Gray et al. |
| 7,122,384 B2 | 10/2006 | Prober et al. |
| 7,123,359 B2 | 10/2006 | Armstrong et al. |
| 7,141,212 B2 | 11/2006 | Catt et al. |
| 7,192,778 B2 | 3/2007 | Natan |
| 7,225,082 B1 | 5/2007 | Natan et al. |
| 7,285,427 B2 | 10/2007 | Williams |
| 7,361,410 B2 | 4/2008 | Zhang et al. |
| 7,443,489 B2 | 10/2008 | Natan |
| 7,501,288 B2 | 3/2009 | Schultz et al. |
| 7,981,695 B2 | 7/2011 | Schultz et al. |
| 2001/0002315 A1 | 5/2001 | Schultz et al. |
| 2002/0142480 A1 | 10/2002 | Natan |
| 2003/0232388 A1 | 12/2003 | Kreimer et al. |
| 2005/0036148 A1 | 2/2005 | Phelan |
| 2005/0037510 A1 | 2/2005 | Sharrock et al. |
| 2005/0037511 A1 | 2/2005 | Sharrock |
| 2009/0161104 A1 | 6/2009 | Schultz et al. |

FOREIGN PATENT DOCUMENTS

| | | |
|---|---|---|
| EP | 1 181 091 | 2/2002 |
| WO | WO 88/07680 | 10/1988 |
| WO | WO 92/17781 | 10/1992 |
| WO | WO 98/04740 | 2/1998 |
| WO | WO 98/10289 | 3/1998 |
| WO | 9837417 A1 | 8/1998 |
| WO | WO 99/21934 | 5/1999 |
| WO | WO 00/11024 | 3/2000 |
| WO | WO 00/27645 | 5/2000 |
| WO | WO 01/25002 | 10/2000 |
| WO | WO 01/25510 | 10/2000 |
| WO | WO 01/08081 | 2/2001 |
| WO | WO 01/25758 | 4/2001 |
| WO | WO 02/29136 | 4/2002 |
| WO | WO 02/68932 | 6/2002 |
| WO | WO 02/079764 | 10/2002 |
| WO | WO 03/021231 | 3/2003 |
| WO | WO 03/021853 | 3/2003 |
| WO | WO 2006/036130 | 4/2006 |
| WO | WO 2006/042111 | 4/2006 |
| WO | WO 2006/105110 | 10/2006 |

OTHER PUBLICATIONS

Hicks, "SERS: Surface Enhanced Raman Spectroscopy", MSU CEM 924, Spring 2001, pp. 1-10.*
Oblonsky and Devine, "A Surface Enhanced Raman Spectroscopic Study of the Passive Films Formed in Borate Buffer on Iron, Nickel, Chromium and Stainless Steel", Corrosion Science, 1995, vol. 37, No. 1, pp. 17-41.*
U.S. Appl. No. 09/598,395, filed Jun. 20, 2000, Natan & Mallouk.
Ascencio et al., Surface Science (2000) 447: 73-80.
Brazdil & Yeager, J. Phys. Chem. (1981) 85: 995-1004.
Byahut & Furtak, Langmuir (1991) 7: 508-513.
Dhere et al., Ultramicroscopy (1985) 18: 415-418.
Duff et al., Angew. Chem. Int. Ed. Eng. (1987) 26: 676-678.
Hall et al., Langmuir (2000) 16: 1454-1456.
Jin et al., Science (2001) 294: 1901-1903.
Kovtyukhova et al., J. Phys. Chem. B (2001) 105: 8762-8769.
Liz-Marzán et al., Langmuir (1996) 12: 4329-4335.
Michaels et al., J. Phys. Chem. B (2000) 104: 11965-11971.
Michaels et al., J. Am. Chem. Soc. (1999) 121: 9932-9939.
Ni et al., Anal. Chem. (1999) 71:4903-4908.
Sun et al., J. Mater. Sci. (2000) 35: 1097-1103.
Switzer et al., J. Am. Chem. Soc. (1998) 120: 3530-3531.
Ung et al., Langmuir (1998) 14: 3740-3748.
Nicewarner, et al., Abstracts of Papers of the American Chemical Society, 1998, 216, P172-COLL.
Shibata et al. (1998) J. Sol-Gel. Technol. 11:279-287.
Felidj et al. (1998) New J. Chem. 725-732.
Freeman et al. (1996) 100:718-724.

(56) References Cited

OTHER PUBLICATIONS

U.S. Appl. No. 09/676,890, Natan et al., Oct. 2, 2000.
U.S. Appl. No. 09/677,198, Natan et al., Oct. 2, 2000.
Akbarian F. et al., "Porous Sol-Gel Silicates Containing Gold Particles as Matrices for Surface-Enhanced Raman Spectroscopy", Journal of Raman Spectroscopy; vol. 27, Issue 10, Oct. 1996, pp. 775-783.
Akerman et al., "Nanocrystal targeting in vivo" PNAS, 99 (20), 2002, p. 12621.
Averitt et al., "A metal nanoshell consists of a nanometer-scale dielectric core surrounded by a thin metallic shell. The plasmon resonance of metal nanoshells displays a geometric tunability", JOSA B, vol. 16, Issue 10, 1999, pp. 1824-1832.
Ballou et al., "Nonivasive imaging of quantum dots in mice", Bioconjugate Chem., 15 (1), 2004, pp. 79-86.
Bruchez et al., "Semiconductor nanocrystals as fluorescent biological labels", Science, Sep. 25, 1998, 281(5385), pp. 2013-2016.
Chan et al., "Quantum dot bioconjugates for ultrasensitive nonisotopic detection", Science, 1998, 281, pp. 2016-2018.
Co-Pending U.S. Appl. No. 11/051,222, filed on Feb. 4, 2005.
Co-Pending U.S. Appl. No. 11/113,601, filed on Apr. 25, 2005.
Co-Pending U.S. Appl. No. 11/132,510, filed on May 18, 2005.
Co-Pending U.S. Appl. No. 11/132,974, filed on May 18, 2005.
Co-Pending U.S. Appl. No. 11/134,129, filed on May 20, 2005.
Co-Pending U.S. Appl. No. 11/134,145, filed on May 20, 2005.
Co-Pending U.S. Appl. No. 11/611,052, filed on Dec. 14, 2006.
Co-Pending U.S. Appl. No. 11/622,915, filed on Jan. 12, 2007.
Co-Pending U.S. Appl. No. 12/245,538, filed on Oct. 3, 2008.
Co-Pending U.S. Appl. No. 12/245,555, filed on Oct. 3, 2008.
El-Kouedi et al., "Optical Properties of Gold-Silver Nanoparticle Pair Structures", J. Phys. Chem. B, 104, 2000, pp. 4031-4037.
Emory et al., "Direct Observation of Size-Dependent Optical Enhancement in Single Metal Nanoparticles", Journal of the American Chemical Society, 1998, 120 (31), 8009-8010.
Emory et al., "Near-Field Surface-Enhanced Raman Spectroscopy on Single Silver Nanoparticles", Analytical Chemistry, 1997, 69 (14), pp. 2631-2635.
Emory et al., "Screening and Enrichment of Metal Nanoparticles with Novel Optical Properties", J. Phys. Chem. B, 1998, 102 (3), pp. 493-497.
European Patent Office, EP Supplementary Search Report prepared Apr. 18, 2008, for European Patent Application No. EP 05 85 6641, 4 pages.
Gao et al., "In vivo cancer targeting, and imaging with semiconductor quantum dots", Nature Biotechnology, 22 (8), 2004, pp. 969-976.
Grabar et al., "Preparation and Characterization of Au Colloid Monolayers", Analytical Chemistry, 1995, 67 (4), pp. 735-743.
Hoadk et al., "Laser-Induced Inter-Diffusion in AuAg Core-Shell Nanoparticles", J. Phys. Chem. B, 2000, vol. 104, pp. 11708-11718.
Horkans et al., "Pulsed Potentiostatic Deposition of Gold from Solutions of the Au(I) Sulfite Complex", Electrochem. Soc., 124, 1977, p. 1499.
Hua-Zhong Yu et al., "Surface-Enhanced Raman Scattering (SERS) from Azobenzene Self-Assembled Sandwiches", Langmuir, vol. 15, No. 1, 1999, pp. 16-19.
Keating et al., "Heightened Electromagnetic Fields Between Metal Nanoparticles: Surface Enhanced Raman Scattering from Metal-Cytochrome c-Metal Sandwiches", J. Phys. Chem. B, vol. 102, No. 47, 1998, pp. 9414-9425.
Keating et al., "Protein: Colloid Conjugates for Surface Enhanced Raman Scattering: Stability and Control of Protein Orientation", J. Phys. Chem. B, vol. 102, No. 47, 1998, pp. 9404-9413.
Kneipp et al., "Approach to Single Molecule Detection Using Surface-Enhanced. Resonance Raman Scattering (SERRS): A Study Using Rhodamine 6G on Colloidal Silver", Applied Spectroscopy, vol. 49, Issue 6, pp. 12A-20A and 691-860, Jun. 1995, pp. 780-784.
Kneipp et al., "Detection and identification of a single DNA base molecule using surface-enhanced Raman scattering (SERS)", Rev. E 57, 1998, pp. R6281-R6284.

Kneipp et al., "Extremely Large Enhancement Factors in Surface-Enhanced Raman Scattering for Molecules on Colloidal Gold Clusters", Applied Spectroscopy, vol. 52, Issue 12, pp. 443A-455A and 1493-1626, Dec. 1998, pp. 1493-1497.
Kneipp et al., "Population Pumping of Excited Vibrational States by Spontaneous Surface-Enhanced Raman Scattering", Phys. Rev. Lett. 76, 1996, pp. 2444-2447.
Kneipp et al., "Single Molecule Detection Using Surface-Enhanced Raman Scattering (SERS)", Phys. Rev. Lett. 78, 1997, pp. 1667-1670.
Kneipp et al., "Single-Molecule Detection of a Cyanine Dye in Silver Colloidal Solution Using Near-Infrared Surface-Enhanced Raman Scattering", Applied Spectroscopy, vol. 52, Issue 2, pp. 72A-73A and 175-321, Feb. 1998, pp. 175-178.
Kneipp et al., "Surface-enhanced Raman scattering: A new tool for biomedical spectroscopy", Current Science, vol. 77, No. 7, Oct. 1999, pp. 915-926.
Kneipp et al., "Ultrasensitive Chemical Analysis by Raman Spectroscopy", Chem. Rev., 1999, 99 (10), pp. 2957-2976.
Kneipp, K., "High-sensitive SERS on colloidal silver particles in aqueous solution", Journal: Experimentelle Technik der Physik; vol. 36, No. 2, 1998, pp. 161-166.
Lyon et al., "Confinement and Detection of Single Molecules in Submicrometer Channels", Analytical Chemistry, 1997, 69 (16), pp. 3400-3405.
Moskovits et al., "SERS and the Single Molecule: Near Field Microscopy and Spectroscopy", SPIE, 2001, vol. 4258, pp. 43-49.
Mucic et al., "DNA-Directed Synthesis of Binary Nanoparticle Network Materials", J. Am. Chem. Soc., 120 (48), 1998, pp. 12674-12675.
Nicewarner Sr. et al., "Synthesis and characterization of well-defined metal nanoparticle-protein-metal nanoparticle sandwiches", Penn State University/University Pk//Pa/16802, Abstracts of Papers of the American Chemical Society, Aug. 23, 1998, vol. 216, 1, pp. 172-COLL.
Nicewarner-Pña et al., "Submicrometer Metallic Barcodes", Science, Oct. 5, 2001, 294, pp. 137-141.
Nie et al., "Probing Single Molecules and Single Nanoparticles by Surface-Enhanced Raman Scattering", Emory, Science, Feb. 21, 1997, vol. 275, No. 5303, pp. 1102-1106.
Nie, S., "Optical detection of single molecules; Annual Review of Biophysics and Biomolecular Structure", vol. 26, 1997, pp. 567-596.
Nikoobakht et al., "Preparation and Growth Mechanism of Gold Nanorods (NRs) Using Seed-Mediated Growth Method", Chem. Mater., 15, 2003, pp. 1957-1962.
Ron et al., "Self-Assembled Monolayers on Oxidized Metals. 2. Gold Surface Oxidative Pretreatment, Monolayer Properties, and Depression Formation", Langmuir, 14 (5), 1998, pp. 1116-1121.
Sandrock et al., "Synthesis and Second-Harmonic Generation Studies of Noncentrosymmetric Gold Nanostructures", J. Phys. Chem. B, 103, 1999, pp. 2668-2673.
Sandrock, "Synthesis and Linear Optical Properties of Nanoscopic Gold Particle Pair Structures", J. Phys. Chem. B, 103, 1999, pp. 11398-11406.
Stöber et al., "Controlled growth of monodisperse silica spheres in the micron size range", Journal of Colloid and Interface Science, vol. 26, Issue 1, Jan. 1968, pp. 62-69.
Van Duyne et al., "Atomic force microscopy and surface-enhanced Raman spectroscopy. I. Ag island films and Ag film over polymer nanosphere surfaces supported on glass", Chem. Phys., vol. 99, Issue 3, pp. 2101-2115.
Vo-Dinh, T., "Surface-enhanced Raman Spectroscopy using metallic nanostructures", Trends in Analytical Chemistry, vol. 17, No. 8-9, 1998, XP002314222.
Walton et al., "Particles for Multiplexed Analysis in Solution: Detection and Identification of Striped Metallic Particles Using Optical Microscopy", Analytical Chemistry, 74 (10), 2002, pp. 2240-2247.
Wasileski et al., "Surface-Enhanced Raman Scattering from Substrates with Conducting or Insulator Overlayers: Electromagnetic Model Predictions and Comparisons with Experiment", Applied Spectroscopy, 2000, vol. 54, pp. 761-772.
Akbarian, F. et al, SPIE 1994, 2288, 140-144.
Betheil, D. et al, Journal of Electroanalytical Chemistry 1996, 409, 137-141.

(56) References Cited

OTHER PUBLICATIONS

Co-Pending U.S. Appl. No. 11/133,926, filed on May 20, 2005.
Grabar, K. C. etal, Langmuir 1996,12, 2353-2361.
Meyer, N. et al, Mikrochimica Acta 2000, 133, 337-339.
Murray, C. A., Journal of the Optical Society of America B: Optical Physics 1985, 2, 1330-1339.
v Hadikar, V. V. et al, Journal of Colloid and Interface Science 2000, 221, 133-136.
Xiao, T. et al, Journal of Physical Chemistry B 1997, 101, 632-638.
Xu, H. et al, Physical Review Letters 1999, 83, 4357-4360.
Xu, M. et al, Journal of Chemical Physics 1992, 96, 7758-7770.
U.S. Appl. No. 09/676,890, Natan et al., filed Oct. 2, 2000.
U.S. Appl. No. 09/677,198, Natan et al., filed Oct. 2, 2000.

* cited by examiner

METHOD OF TAGGING MATERIALS WITH SURFACE-ENHANCED SPECTROSCOPY-ACTIVE SANDWICH PARTICLES

CROSS-REFERENCE TO RELATED APPLICATIONS

This application is a continuation of U.S. application Ser. No. 11/051,222, "Surface-Enhanced Spectroscopy-Active Sandwich Nanoparticles," filed Feb. 4, 2005, which is a continuation of U.S. application Ser. No. 10/056,808, "Surface-Enhanced Spectroscopy-Active Sandwich Nanoparticles," filed Jan. 25, 2002, now U.S. Pat. No. 6,861,263, issued Mar. 1, 2005, which claims the benefit of U.S. Provisional Application No. 60/264,497, "Nanoparticle Tags Comprising Sandwiches of SERS-Active Particles," filed Jan. 26, 2001; and U.S. Provisional Application No. 60/297,097, "Method for Preparing SERS Sandwich Geometries from Striped, Rod-Shaped Nanoparticles," filed Jun. 8, 2001. All of the foregoing are herein incorporated by reference in their entirety.

FIELD OF THE INVENTION

The present invention relates generally to nanoparticles used as molecular tags in biological assays and other applications. More particularly, it relates to surface-enhanced spectroscopy-active (e.g., SERS-active) nanoparticles containing Raman-active material sandwiched between two SERS-active layers.

BACKGROUND ART

When light is directed onto a molecule, the vast majority of the incident photons are elastically scattered without a change in frequency; however, the energy of some of the incident photons (approximately 1 in every $10^7$ incident photons) is coupled into distinct vibrational modes of the molecule's bonds. Such coupling causes some of the incident light to be inelastically scattered by the molecule with a range of frequencies that differ from the range of the incident light. This is termed the Raman effect. By plotting the frequency of such inelastically scattered light against its intensity, the unique Raman spectrum of the molecule under observation is obtained. Analysis of the Raman spectrum of an unknown sample can yield information about the sample's molecular composition.

The incident illumination for Raman spectroscopy, usually provided by a laser, can be concentrated to a small spot if the spectroscope is built with the configuration of a microscope. Since the Raman signal scales linearly with laser power, light intensity at the sample can be very high in order to optimize sensitivity of the instrument. Moreover, because the Raman response of a molecule occurs essentially instantaneously (without any long-lived highly energetic intermediate states), photobleaching of the Raman-active molecule—even by this high intensity light—is impossible. This places Raman spectroscopy, in stark contrast to fluorescence spectroscopy, in which photobleaching dramatically limits many applications.

The Raman effect can be significantly enhanced by bringing the Raman-active molecule(s) close (<50 Å) to a nanometer-scale roughened metal surface. Bringing molecules in close proximity to metal surfaces is typically achieved through adsorption of the Raman-active molecule onto suitably roughened gold, silver, or copper or other free electron metals. Surface-enhancement of the Raman activity is also observed with metal colloidal particles, metal films on dielectric substrates, and metal particle arrays. The mechanism by which this surface-enhanced Raman scattering (SERS) occurs is not well understood, and is thought to result from a combination of (i) electromagnetic effects, surface plasmon resonances in the metal that enhance the local intensity of the light, and (ii) chemical effects, formation and subsequent transitions of charge-transfer complexes between the metal surface and the Raman-active molecule.

SERS allows detection of molecules attached to the surface of a single gold or silver nanoparticle. A Raman-enhancing metal that has associated or bound to it a Raman-active molecule(s) is referred to as a SERS-active nanoparticle. Such SERS-active nanoparticles can have utility as optical tags. For example, SERS-active nanoparticles can be used in immunoassays when conjugated to an antibody against a target molecule of interest. If the target of interest is immobilized on a solid support, then the interaction between a single target molecule and a single nanoparticle-bound antibody can be detected by searching for the Raman-active molecule's unique Raman spectrum. Furthermore, because a single Raman spectrum (from 100 to 3500 $cm^{-1}$) can detect many different Raman-active molecules, different SERS-active nanoparticles can be used in multiplexed assay formats.

In U.S. patent application Ser. No. 09/680,782, filed Oct. 6, 2000, entitled "Surface Enhanced Spectroscopy-Active Composite Nanoparticles," incorporated herein by reference in its entirety, and hereinafter referred to as the '782 application, SERS-based tags are described. Each SERS-active composite nanoparticle (SACN) consists of a SERS-active metal nanoparticle; a submonolayer, monolayer, or multilayer of SERS-active species in close proximity to the metal surface; and an encapsulating shell consisting of a polymer, glass, or other dielectric material. This places the SERS-active molecule (alternately referred to herein as the "analyte," not to be confused with the species in solution that is ultimately being quantified) at the interface between the metal nanoparticle and the encapsulant. In other words, "analyte" as used in the specification is not the species that are tagged by the SACNs (which would be the conventional usage), but the one or more spectroscopy-active (e.g., Raman-active) molecules attached to or associated with the metal nanoparticles themselves. Because it is the signal from the SES-active composite nanoparticle that is being detected and measured, the Raman-active molecules of the composite nanoparticles themselves are referred to as the analyte. This special definition has been chosen by the applicant to underscore that it is the Raman spectrum of the Raman-active molecules, rather than the item tagged or labeled by the SACN, that is the source of the signal being measured.

The analyte molecule can be chosen to exhibit extremely simple Raman spectra, because there is no need for the species to absorb visible light. This, in turn, allows multiple SACN particles, each with different analyte molecules, to be fabricated such that the Raman spectra of each analyte can be distinguished in a mixture of different types of SACN particles.

SACNs are easily handled and stored. Because of the encapsulant, they are also aggregation resistant, stabilized against decomposition of the analyte in solvent and air, chemically inert, and easily centrifuged and redispersed without loss of SERS activity. Most importantly, the encapsulant shells of SACNs may be readily derivatized by standard techniques. This allows SACNs to be conjugated to molecules (including biomolecules such as proteins and nucleic acids) or to solid supports without interfering with the Raman activity of the SACNs. Unlike metal nanoparticles, SACNs can be evaporated to dryness, and then completely redispersed in solvent. Using the techniques provided in the '782 application, it is possible to fabricate SACNs that are individually detectable using SERS.

The SACNs provided by the '782 application are uniquely identifiable nanoparticles. They can be used in virtually any situation in which it is necessary to label molecules or objects (including beads and other types of solid support) with an optical tag. Biomolecules can be conjugated readily to the exterior of SACNs by standard techniques, thereby allowing the particles to function as optical tags in biological assays. SACNs can be used in virtually any assay that uses an optical tag such as a fluorescent label; however, as optical tags, SACNs have several distinct advantages over fluorescent labels. These advantages include vastly more sensitive detection, chemical uniformity, and the resistance of the SERS activity to photobleaching or photodegradation. A further benefit of using SACNs as optical tags is the ease with which individual SACNs having different SERS activities may be resolved from one another. At least twenty different SACNs are resolvable from one another using a simple Raman spectrometer. This enables multiplexed assays to be performed using a panel of different SACNs, each having a unique and distinguishable SERS activity.

U.S. Pat. No. 6,149,868, entitled "Surface Enhanced Raman Scattering From Metal Nanoparticle-Analyte-Noble Metal Substrate Sandwiches," incorporated herein by reference in its entirety, and hereinafter referred to as the '868 patent, teaches that the Raman intensity of SERS-active molecules can be significantly enhanced by conjugating the molecule to colloidal metal nanoparticles, and then absorbing or covalently-attaching the metal nanoparticles to a macroscopic SERS substrate, such as an aggregated Ag sol or a roughened Ag electrode. In doing so, sandwiches are formed between the metal nanoparticle and the macroscopic SERS substrate, with the SERS-active molecule lying between the two metal surfaces. It is known that the enhancement in SERS-activity in this configuration results from large increases in the electric field between the colloidal metal nanoparticles and the macroscopic SERS substrate. Although the sandwiches of the '868 patent are themselves useful as SERS substrates, the macroscopic dimensions of the SERS-active substrate onto which the nanoparticles are absorbed preclude them from being optimal optical tags for biomolecular labeling. Moreover, the structural heterogeneity of the SERS-active substrates onto which the colloidal particles are absorbed means that a sandwich is not formed at every site where a colloidal particle associates with the SERS-active substrate.

Recently, SERS spectra have been observed for single molecules on the surface of colloidal metal nanoparticles, with enhancement factors of $10^{14}$-$10^{15}$. Although the mechanisms for single-molecule and single-particle SERS are still unknown, it is believed that the large enhancement factors are obtained only at the interstitial sites between two particles or at locations outside sharp surface protrusions, so-called "hot spots." In fact, it has been hypothesized that SERS spectra of large numbers of molecules are dominated by single molecules adsorbed at special surface sites. One recent study of SERS of rhodamine 6G molecules on the surface of silver nanoparticles found that SERS activity occurred only for clusters of at least two individual silver particles, and not for isolated particles (A. M. Michaels et al., "Ag Nanocrystal Junctions as the Site for Surface-Enhanced Raman Scattering of Single Rhodamine 6G Molecules," *J. Phys. Chem. B* 2000, 104, 11965-11971). These clusters were not deliberately prepared, but rather were formed randomly by spin-casting a solution of R6G and colloidal silver onto a polylysine-coated quartz cover slip. In addition, there were no free clusters of particles formed; all of the clusters were formed on the surface of the cover slip.

Rod-shaped nanoparticles and methods for their use are described in detail in U.S. patent application Ser. No. 09/598,395, filed Jun. 20, 2000, and its continuation-in-part, U.S. patent application Ser. No. 09/677,198, filed Oct. 2, 2000, both entitled "Colloidal Rod Particles as Nanobar Codes," and both incorporated herein by reference in their entirety. Also incorporated herein by reference in their entirety are U.S. patent application Ser. No. 09/677,203, entitled "Method of Manufacture of Colloidal Rod Particles as Nanobar Codes," and U.S. patent application Ser. No. 09/676,890, "Methods of Imaging Colloidal Rod Particles as Nanobar Codes," both filed Oct. 2, 2000. The latter application describes flow cytometry techniques to quantify fluorescent nanoparticles, optical microscopy fluorescence detection of nanoparticles, and TEM reflectivity detection of nanoparticles. Also incorporated herein by reference in its entirety is U.S. patent application Ser. No. 09/969,518, "Method of Manufacture of Colloidal Rod Particles as Nanobarcodes," filed Oct. 2, 2001, which discloses photolithographic methods for manufacturing the rod-shaped nanoparticles.

Similar structures have been formed as nanowires for use in electronic applications. For example, nanowire diodes have been synthesized by sequential electroplating of metals and assembly of semiconductor/polymer films (N. I. Kovtyukhova et al., "Layer-by-Layer Assembly of Rectifying Junctions in and on Metal Nanowires," *J. Phys. Chem. B* 2001, 105, 8762-8769). These diodes consist of 10-nm thick semiconductor/polymer films sandwiched between two 0.5-300 µm segments of a 200-nm diameter nanowire. These particles are too large to be SERS active. Much smaller 30-nm diameter nanowires have also been produced containing alternating 5-nm thick Ni and Cu layers (L. Sun et al., "Fabrication of Nanoporous Single Crystal Mica Templates for Electrochemical Deposition of Nanowire Arrays," *J Mater. Sci.* 2000, 35, 1079). These nanowires are not SERS-active and are not used as biomolecular or other tags.

Given the dramatic enhancement of SERS activity observed when a Raman-active molecule is sandwiched between two SERS-active substrates, it is desirable to have a method for deliberately preparing such sandwiches. Particles prepared with such methods would have utility as optical tags.

SUMMARY OF THE INVENTION

The present invention provides free-standing SERS-active nanoparticles that can be deliberately prepared and can be used as optical tags. The particles display a sandwich-type geometry consisting of at least three elements: at least two surface-enhanced spectroscopy-active (e.g., SERS-active) outer regions and a spectroscopy-active (e.g., Raman-active) analyte positioned between the outer regions. Because of the large enhancement factors associated with such a sandwich structure, high signal intensities are obtained from even sub-monolayer analytes, and the particles can be used in standard assays in which fluorescent tags are currently used.

Preferably, the nanoparticles have a maximum length of at most 300 nm and are rod shaped. The outer regions each have a maximum length of less than 200 nm and preferably less than 100 nm, and can have the same or different chemical composition. Typically, the outer regions contain a metal such as Au, Ag, Cu, Na, K, Cr, Al, or Li. The spacing between the outer regions is selected to maximize the intensity of a spectrum of the analyte, and can be controlled by one or more spacers placed between the analyte and the outer regions. The analyte ranges from a monolayer to a multi-layer of molecules, with a preferable thickness of up to 50 nm, and most preferably between 0.5 and 2 nm. The entire particle is preferably surrounded by an encapsulant to which a capture molecule can be attached.

The present invention also includes a collection or ensemble of these differentiable nanoparticles. Preferably, the members of the collection are differentiable based on the nature of the Raman spectrum generated by the intermediate layer. When the particles have attached capture molecules, the analytes encode the identity of the capture molecules.

The present invention also includes methods of manufacture of the nanoparticles and applications for their use. The nanoparticles may be used in virtually any application or assay in which a detectable tag or label is required, particularly biological assays that typically use fluorescent tags attached to biomolecules. In these applications, one or more particles are attached to an object of interest such as a biomolecule, and a spectrum is acquired of the particle. In a method for conducting an assay, ligands capable of associating with an analyte in solution are attached to the particles to form coated particles, and the coated particles are contacted with the solution. Typically, particles having different Raman spectra are attached to different ligands, which are capable of associating with different analytes.

DETAILED DESCRIPTION OF THE INVENTION

The present invention is directed to surface enhanced spectroscopy-active nanoparticles that display a sandwich-type geometry. Also included within the scope of this invention are methods of manufacture of the particles and uses of the particles, including their use as molecular or cellular optical tags. For clarity, the method is described primarily in reference to surface-enhanced Raman spectroscopy (SERS); however, it is to be understood that the method can be used with any of the different spectroscopies described below.

Figure 1:
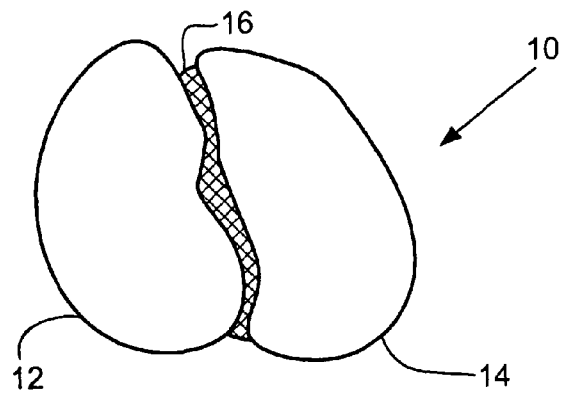
FIG. 1 is a schematic cross-sectional view of a SERS sandwich nanoparticle (SSN) of the present invention.

FIG. 1 illustrates a basic embodiment of a nanoparticle 10 of the invention displaying a sandwich geometry containing two outer regions or layers 12 and 14 and an intermediate region or analyte 16. Nanoparticles with a sandwich geometry are referred to as "SERS sandwich nanoparticles" or "SSNs." Throughout this application, the composition of a SSN is described as X/Y/Z, where X and Z signify the composition of the outer regions and Y signifies the intermediate region composition. The outer regions 12 and 14 of SSNs contain SERS-active entities, and the intermediate region 16 contains a substance with a Raman spectrum, referred to as a Raman-active substance. SERS-active entities enhance the intensity of the Raman signal of analytes in contact with the SERS-active entities, in this case the intermediate layer 16. In preferred embodiments, each outer region is formed by a discrete SERS-active particle. For example, a sandwich can be formed between two 5-nm Au particles, with the intermediate layer lying at the point of contact of the two particles. In use, the nanoparticles of the invention are not fixed to a surface and are therefore referred to as free-standing particles. As used herein, a free-standing particle refers to one that can be removed from solution and resuspended; an aggregated colloidal sol, for example, is not a free-standing particle.

The particles forming the outer regions 12 and 14 of the structure are characterized by a length dimension whose nature depends upon the particular shape of the particle. For example, spherical particles are characterized by a diameter and cylindrical particles by a longitudinal length. In general, for irregularly shaped particles, the length dimension is defined as the longest distance between two points on the surface of the particle. The smallest SERS-active particles that are useful to form the sandwich structures of the invention are those that exhibit bulk metallic properties, e.g., those at least 3 nm in one or more dimensions, but that are smaller than the wavelength of incident light. Preferably, the maximum length dimension of the particles is approximately 200 nm, more preferably 150 nm, and most preferably 100 nm. It is not necessary that the outer layers of a single SSN contain particles of the same size. For example, a sandwich structure of 10-nm diameter particle/SERS-active molecule/100-nm diameter particle is within the scope of the invention. Preferably, the entire SSN has a maximum length dimension of at most 300 nm.

Figure 2:
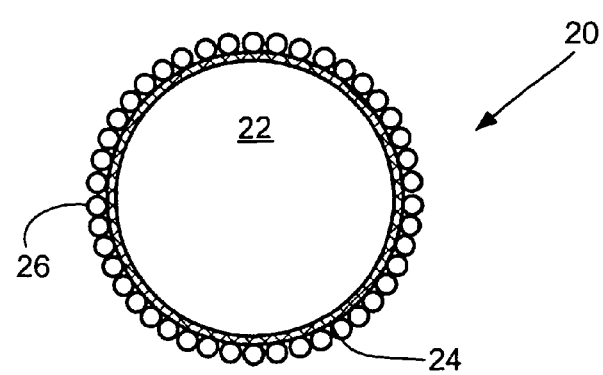
FIG. 2 is a schematic cross-sectional view of an alternative embodiment of a SSN having multiple sandwich structures.

In some embodiments, an individual SSN is constructed from just two SERS-active particles or regions. For example, as in FIG. 1, a SSN can contain an intermediate layer sandwiched between two 5-nm particles; in this example, just one instance of the sandwich geometry is found. In other embodiments, a SSN contains multiple outer layers such that multiple instances of the sandwich geometry are found on a single SSN. For example, as illustrated in FIG. 2, a SSN 20 can be formed with the following structure: a 200-nm diameter particle 22 coated with an intermediate layer 24, and then coated with a layer 26 of 10-nm particles. In this embodiment, the sandwich geometry is found at each location where a 10-nm particle is associated with the 200-nm particle 22.

The SERS-active materials that form the outer regions of the sandwich preferably contain those metallic substances for which chemical enhancement, electromagnetic enhancement, or both, is known in the art. Preferably, the outer regions contain Au, Ag, or Cu. The outer regions can also contain other metals, including, but not limited to, Na, K, Cr, Al, or Li. Furthermore, the outer regions can contain alloys of metals. In some embodiments, each outer region particle consists of a core (of pure metal or an alloy) overlaid with at least one metal shell. Preferably, the composition of the outer layers is chosen to maximize the intensity of the Raman signal from the intermediate layer.

The outer regions of a SSN can be formed by SERS-active particles of the same chemical composition, e.g., Ag/intermediate layer/Ag. Alternatively, the outer layers can have different compositions, e.g., Au/intermediate layer/Ag. In still further embodiments, SSNs in which multiple instances of the sandwich geometry occur can be organized in such a way that different outer regions are present at different locations on the same SSN. For example, a 200-nm Au particle can be coated first with an intermediate layer and then with a mixture of 10-nm Ag particles and 10-nm Au particles. The resulting SSN displays both Ag/intermediate layer/Au and Au/intermediate layer/Au sandwich geometries.

The SERS-active particles that form the outer layers of a SSN can have a variety of shapes and sizes. Particle shapes that can be used for SSNs include, but are not limited to, spheres, oblate (pancake-shaped) and prolate (cigar-shaped) spheroids, lacunar (recessed) shapes, hollow shapes (e.g., straw shaped), cylindrical particles, cubic particles, or rectangular particles. In addition, outer layer particles can have a concave or convex shape (e.g., like optical lenses). Alternatively, particles can have a tipped shape (like the end of pencil or like a pyramid). Particle shapes can also be chosen such that particles fit together. For example, if each outer region contains a serrated feature with teeth, then individual particles can interlock by meshing the teeth.

Figure 3:
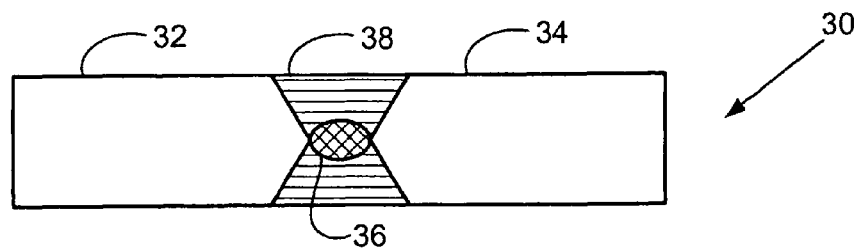
FIG. 3 is a schematic cross-sectional view of an embodiment of a SSN having tipped outer regions.

FIG. 3 illustrates an embodiment of a SERS sandwich particle 30 in which the outer regions 32 and 34 have a tipped shape, with their points directed toward each other. The analyte 36, which can be a single molecule, is positioned between the two tips, i.e., at the point of smallest distance between the two outer regions 32 and 34. Adjacent to the analyte 36 and filling the space between the outer regions 32 and 34 is a spacer material 38 that can be the same as or different from the analyte 36. If the material 38 is different from the analyte 36, it is preferably a material that does not yield a measurable Raman spectrum.

Numerous other well-defined shapes have been reported for colloidal noble metal particles, including but not limited to truncated icosahedra, as described by Ascencio et al., *Surface Science* 2000, 447, 73, incorporated herein by reference in its entirety. Additional examples of particle shapes include but are not limited to twinned crystals described in Dhere et al., *Ultramicroscopy* 1985, 18, 415-418; shapes described in Duff et al., *Angew. Chem. Int. Ed. Eng.* 1987, 26, 676-678; and prisms described in R. Jin et al., *Science* 2001, 294, 1901-1903; all of which are incorporated herein by reference in their entirety. Moreover, in addition to particle shape, the extent of SERS activity is dependent on the excitation wavelength and the manner of surface preparation.

In the preceding embodiments, outer regions have well-defined shapes; however, outer regions that lack a definable overall structure, but have at least one definable feature, are included within the scope of the invention. A non-limiting example is the shape of a crumpled piece of paper: this has no well-defined shape, but possesses well-defined features, such as a square pyramid, on its otherwise indefinable surface. Similarly, particles that have such features on an otherwise well-defined shape are also included within the scope of the invention. A non-limiting example is the presence of a square pyramidal tip on the surface of an otherwise perfect sphere. Those skilled in the art will recognize that such features have often been described as being important in the mechanism of SERS (the so-called "antenna" effect). Accordingly, it is to be understood that any and all particles with one or more definable features on their surfaces are included in the scope of the invention. In addition, in preferred embodiments of the invention, the composition, shape, and size of the outer layer particles are chosen to optimize the intensity of the Raman spectrum of the intermediate layer.

Figure 4:
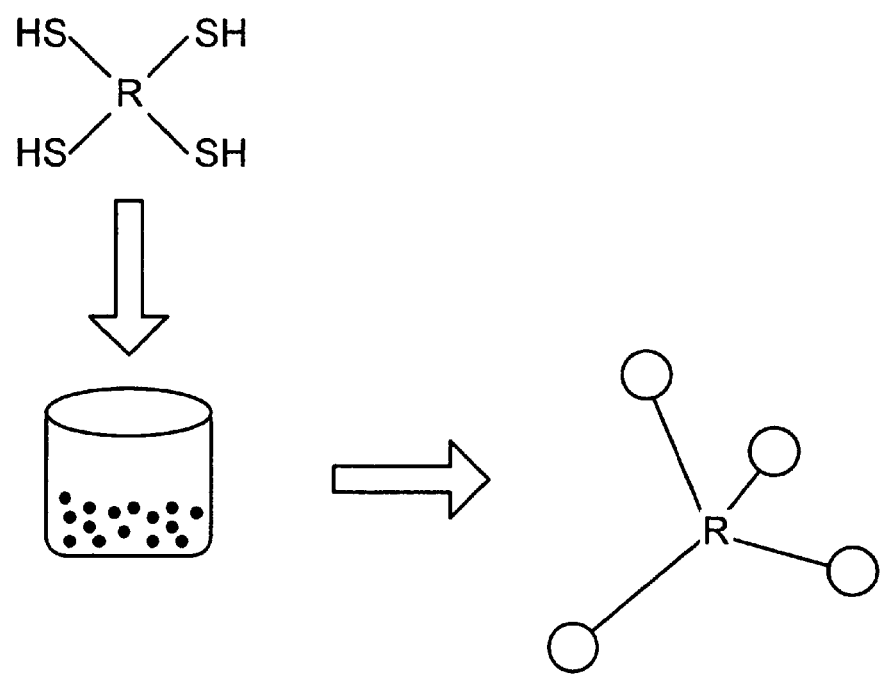
FIG. 4 illustrates a self-assembled SSN having multiple outer regions.

In some embodiments, SSNs are formed by self-assembly and can have more than two outer regions. For example, as shown in FIG. 4 (not to scale), an analyte molecule R can be prepared linked to four thiol groups. When added to a gold colloid solution, each thiol group binds to a single gold colloid, forming the tetrahedral sandwich structure shown in FIG. 4. This concept can be extended to any number of colloids surrounding the analyte. For example, the analyte can be linked to one or more dendrimers, synthetic three-dimensional branched macromolecules. Each branch of the dendrimer can terminate with a thiol group, causing self-assembly of a corresponding number of gold colloids around the analyte.

The spacing between the outer regions is preferably chosen in order to maximize the intensity of the Raman spectrum of the material in the intermediate layer. Because the electromagnetic field strength between the outer regions is a function of the particle shape and size, optimal spacing is specific to a given SSN. Typically, the field is strongest at the center of the distance between the two outer regions. This distance is lowest when the outer layers touch one another. It is possible to increase the distance between the outer layers if one, or preferably both, of the outer regions are coated with a layer of a material such as metal oxide or glass oxide. The oxide layer serves as a spacer; by modifying the thickness of the oxide layer, the distance between the outer layers can be "tuned" to arrive at the distance at which the most intense Raman spectrum is obtained from the intermediate layer material. The spacer layer can instead be a biological molecule, such as an antibody, attached to the outer layer and capable of binding to the Raman-active analyte. Preferably, the intermediate layer is a monolayer of Raman-active molecules, with a thickness ranging between 0 and 50 nm, and preferably approximately 0.5-2 nm. It can also be as small as a single molecule or as large as a multi-layer of Raman-active molecules.

Figure 5:
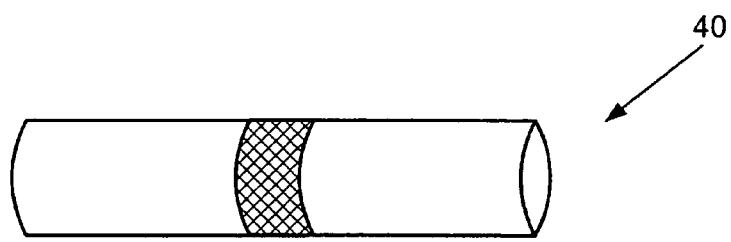
FIG. 5 is a schematic perspective view of a preferred embodiment of a rod-shaped SSN of the present invention.

In preferred embodiments, SSNs are organized as segmented rod nanoparticles 40, shown in FIG. 5. Rod-shaped nanoparticles and methods for their manufacture are described in the above-referenced patent applications. Segmented rod-shaped nanoparticles, referred to as Nanobarcodes™ particles, preferably contain multiple segments or "stripes" of metal; however, the segments can consist of any material. Such Nanobarcodes™ particles can be fabricated by the sequential electrochemical reduction of metal ions in solution using a porous membrane as a template. In this method, particles are formed one stripe at a time within the pores of the membrane. Segments can also be added using, for example, chemical vapor deposition and/or chemical self assembly. Using the aforementioned methods, it is possible to form Nanobarcodes™ particles of length between 10 nm and 50 μm and of width between 5 nm and 50 μm, with any cross sectional shape. In the instant invention, SNNs can be formed as rod-shaped particles in which the outer regions and the intermediate region are each individual stripes or segments. Rod-shaped SSNs have preferred dimensions of between 10 and 100 nm in diameter and 100 and 200 nm in length.

For example, a rod-shaped particle with a stripe of Raman-active material sandwiched between two stripes of Ag functions as a SSN. This particle has the basic SSN architecture, namely outer region/intermediate layer/outer region. Similarly, a 5-stripe particle of composition Ag/oxide spacer/intermediate layer/oxide spacer/Ag also serves as a SSN. Using the Nanobarcodes particle fabrication techniques, it is possible to form SSNs that comprise multiple outer layers and multiple intermediate layers within a single particle. In such particles, each intermediate layer stripe is flanked by outer layer stripes, preferably separated from the intermediate layer by stripes of oxide spacers. A non-limiting example of this embodiment is the rod-shaped particle of composition Ag/intermediate layer/Ag/intermediate layer/Ag.

Although Nanobarcodes particle technology is typically used to make nanoparticles with a circular cross-section, the methods can be adapted to form nanoparticles with any cross-sectional shape. For example, in some embodiments, SSNs formed as Nanobarcodes particles can have ends that are sharp-tipped, e.g., spiked or pencil tipped. The presence of such sharp-tipped features is known to contribute to the surface enhancement of the Raman spectrum through the "antenna effect" mentioned above. In another embodiment, a Nanobarcodes particle can be formed with the architecture of an optical microcavity.

In preferred embodiments of the invention, SSNs are used as tags or labels that can be physically or chemically (covalently or non-covalently) attached to entities of interest (ranging in size from molecules to macroscopic) for the purpose of quantification, identification, and/or tracking. Ligands or capture molecules capable of associating with or binding to analytes of interest are attached to the surface of the SSNs. In these embodiments, the Raman spectrum of the intermediate layer serves, at least in part, to identify the capture molecules. When SSNs are used as tags or labels, the intermediate layer is referred to alternately as the "analyte," not to be confused with the species or object that is ultimately being quantified using SSNs as tags or labels. Any and all conditions leading to differentiation of particles on the basis of Raman spectroscopy can be used to make sets of nanoparticulate tags.

When the SSNs are Nanobarcodes particles, the intermediate layer is preferably between 0 and 50 nm, and most preferably between 0.5 and 2 nm in thickness. The simplest analyte species contemplated by the invention is a monolayer, submonolayer, or fraction of a single monolayer of a single molecular or ionic species. For example, a SSN including Ag particle/single molecular layer of pyridine/Ag particle gives the SERS spectrum of the pyridine layer. Preferred intermediate layers include aromatic heterocyclic molecules (e.g., pyridine) and their derivatives, Raman-active polymers, or bifunctional molecules such as diisocyanate, which binds tightly to gold. Depending on the magnitude of the enhancement, a single molecule may suffice. In other words, the analyte amount can be as little as one molecule. As described above, Raman spectra have been obtained for single molecules at the junction between two SERS-active particles.

The characteristics of preferred analytes (from the perspective of SERS) are (i) strongly Raman-active, and (ii) exhibiting a simple Raman spectrum. The first criterion is important because the greater the Raman activity, the fewer the number of molecules needed, and the less stringency required for the outer SERS-active regions. The second criterion is important because the simpler the Raman spectrum, the greater the number of unique SSNs that can be generated and used simultaneously. At 633 nm, it is possible to form 540 distinct and easily resolvable peaks in a single Raman spectrum from 300 to 3000 cm$^{-1}$ using a spectrograph to spread photons and a charge coupled device (CCD) camera as a detector. If each peak represents a unique analyte, then it is possible to generate a panel of 540 differentiable SSNs.

Practice of the invention is not limited to the above-described instrumentation: Raman experiments with SSNs can be carried out with visible or near-IR irradiation, make use of Raman bands from 300 cm$^{-1}$ to 3300 cm$^{-1}$, employ any form of monochromator or spectrometer to spatially or temporally resolve photons, and any form of photon detector. This arrangement facilitates the synthesis of panels of at least 10 resolvable SSNs, and provides ample bandwidth for literally hundreds of panels of SSNs.

Those skilled in the art will recognize that there is a great deal of latitude in the composition of an analyte that yields a distinct Raman spectrum. For example, in some embodiments, the analyte is a positively or negatively charged ion (e.g., Na$^+$ or CN$^-$). If the analyte is a molecule, it can be neutral, positively charged, negatively charged, or amphoteric. Species such as metals, oxides, sulfides, etc. can serve as Raman-active species. Any species or collection of species that gives rise to a unique Raman spectrum can serve as the species attached to or associated with the SES active composite nanoparticle. Examples easily number in the many millions and include but are not limited to Hg, dimethylformamide, HCl, H$_2$O, polypyrrole, hemoglobin, oligonucleotides, charcoal, carbon, sulfur, rust, polyacrylamide, citric acid, and diamond. In the case of diamond, the unique phonon mode of the particle can be used. For hemoglobin, only the porphyrin prosthetic group exhibits significant Raman activity; thus, complex substances can be used as the species attached to or associated with the SES active composite nanoparticle even if only part of the molecular or atomic complexity is present in the Raman spectrum.

The analyte can also be a polymer to which multiple Raman-active moieties are attached. In this case, differentiable SSNs contain the same polymer serving as the intermediate layer, but the polymers have different attached moieties yielding different Raman spectra. The polymer backbone does not itself contribute to the acquired Raman spectrum. In one embodiment, the polymer is a linear chain containing amine groups to which Raman-active entities are attached. Alternatively, the polymer can be a dendrimer, a branched polymer with a tightly controlled tree-like structure, with each branch terminating in a Raman-active species. A suitable dendrimer structure has four generations of branches terminating in approximately 45 Raman-active entities.

In some embodiments, the invention contemplates the use of Raman-active analytes with distinct isotopic compositions. For example, the analyte $^{13}$CN is easily distinguished by Raman spectroscopy from the analyte $^{12}$CN, and also from the analyte C$^{15}$N. Furthermore, the use of analytes that have isotopic compositions distinct from naturally abundant species allows analytes to be resolved from background Raman activity. Hence, the analyte $^{13}$CN is resolvable from any natural $^{12}$CN present in the background.

It should likewise be clear to those skilled in the art that SSNs that give rise to unique Raman spectra can be considered different even if the analyte is essentially the same. For example, the Raman spectrum of a cationic polymer charge compensated by anions can change depending on the choice of counter ion. A panel of differentiable SSNs can be formed using this polymer as a component of the analyte; each unique SSN has the polymer charge-compensated by a different anion, thereby endowing each SSN with a unique Raman spectrum. In addition, a given analyte may have different Raman shifts on different SERS-active layers, and differentiable SSNs can be formed using the same analyte sandwiched between layers of different metals. For example, p-nitroso-N,N'-dimethylaniline (p-NDMA) has different Raman shifts on gold and silver surfaces (J. F. Brazdil and E. B. Yeager, *J. Phys. Chem.* 1981, 85, 995-1004, and S. Byahut and T. E. Furtak, Langmuir 1991, 7, 508-513).

Alternatively, one or more bands in the Raman spectrum of an analyte may be dependent on the density of the analyte in the SSN. SSNs formed with different densities of the same analyte are therefore differentiable from one another.

While the examples above have focused on Raman scattering, and in particular surface enhanced Raman scattering (SERS), those practiced in the art of Raman spectroscopy are aware that the general concept of inelastic light scattering has many alternative manifestations that can be used for detection. The basic "normal" Raman scattering experiment involves detection/measurement of Stokes-shifted photons, i.e., those with a lower energy than the incident photons. Anti-Stokes photons—those with energies greater than the incident photons—are also generated in a Raman experiment. While the intensity of anti-Stokes Raman bands is typically low compared to the Stokes bands, they offer one very significant advantage: the lack of interference from fluorescence, which by definition occurs at lower energies than excitation. In embodiments in which the overall SERS intensity is sufficiently high, this may be an attractive method for the detection of SSNs.

For molecules whose absorption spectrum overlaps with the laser excitation wavelength, Raman experiments are said to be in resonance; both the theory and practice of resonance Raman are well understood. SERS experiments carried out under these circumstances are referred to as SERRS (surface enhanced resonance Raman scattering). SERRS spectra are typically more intense than normal Raman spectra, and may provide an additional benefit. Organic molecules that possess high extinctions in the visible region of the spectrum also exhibit relatively complex molecular structures, and as such might not be optimal choices for the intermediate layer. On the other hand, coordination complexes can have reasonably high absorptivity and still possess simple structures. For example, simple homoleptic complexes of Cu(I) and Cu(II) are often intensely colored (e.g., $[Cu(NH_3)_4]^+$).

In addition to SERS and SERRS, there are a variety of other detection mechanisms contemplated by the instant invention, including but not limited to surface enhanced infrared absorption spectroscopy (SEIRA), surface enhanced hyperRaman spectroscopy (SEHRS), and its resonant analog, SEHRRS. In SEHRS and SEHRRS, two photons of frequency A generate a scattering event at a frequency of 2 A. The primary benefit of this method is the total lack of interference by fluorescence or any other background process: one can excite a particle with 800 nm light and observe photons Raman-shifted from 400 nm. In general, for a given analyte with N atoms, there are either 3N-5 or 3N-6 unique vibrations; all of these vibrations can be found in either the Raman, hyperRaman, or infrared spectrum. Indeed, in some embodiments, identification of SSNs can rest on a combination of optical interrogation methods, including methods that rely on inelastic scattering of photons (e.g., SERS, SERRS, SEHRS, and SEHRRS, in both Stokes and anti-Stokes modes), methods that rely on elastic scattering of photons (e.g., Raleigh scattering and hyperRaleigh scattering for particles with dimensions at least 1/10th of the excitation wavelength), and methods that rely on adsorption, e.g., SEIRA.

In an alternative embodiment of the invention, the SSN (including SSNs formed as Nanobarcodes particles) is coated with an encapsulant. Preferably, the encapsulant does not measurably alter the SERS activity of the naked SSN. However, the advantages of the present invention are still achieved if the encapsulant has some measurable effect, provided it does not interfere with the SERS activity or does not add significant complexity to the Raman spectrum. In addition, for biological applications, the encapsulant can be readily modified in order to attach molecules, including biomolecules, to its exterior surface: Suitable encapsulants include, but are not limited to, glasses, polymers, metals, and metal oxides (such as $TiO_2$ and $SnO_2$). The encapsulation is preferably carried out after formation of the SSN. In this way, the Raman-active analyte is sequestered from the surrounding solvent. Such a configuration provides an SSN with stable SERS activity. An additional benefit of encapsulation is that the aggregation of SSNs is minimized. In some cases, the encapsulant and the Raman-active analyte can be of the same material.

In especially preferred embodiments, the encapsulant is glass (e.g., $SiO_x$) or a glasslike substance. To encapsulate in glass, the SSN is preferably treated first with a glass primer (that is, a material that can lead to growth of a uniform coating of glass, or can improve adhesion of the glass coat to the particle, or both). Glass is then grown over the metal nanoparticle by standard techniques well known in the art.

Note that glass and many other materials contain functional groups amenable to molecular attachment. For example, immersion of glass in base allows covalent attachment of alkyl trichlorosilanes or alkyl trialkoxysilanes, with additional functionality available on the end of the alkyl group. Thus, glass surfaces can be modified with all forms of biomolecules and biomolecular superstructures including cells, as well as oxides, metals, polymers, etc. Likewise, surfaces of glass can be modified with well-organized monomolecular layers. In short, glass coatings support essentially any and all forms of chemical functionalization (derivatization). This is equally true for many different forms of encapsulant. As a result, encapsulated SSN particles can be affixed to any species with chemically reactive functionality. All chemical functional groups are reactive under certain conditions. There is thus no limitation to the species that can be immobilized on the encapsulant surface.

The thickness of the encapsulant can easily be varied depending on the physical properties required of the SSN. For example, coatings that are too thick—on the order of 1 micron or more—might preclude obtaining intense Raman spectra. Coatings too thin might lead to interference in the Raman spectrum of the analyte by the molecules on the encapsulant surface. At the same time, physical properties such as sedimentation coefficient are clearly affected by the thickness of the encapsulant. In general, the thicker the encapsulant, the more effective the sequestration of the Raman-active analyte(s) or SSN from the surrounding solvent. When glass is used as the encapsulant, the preferred thickness ranges from 0.5 to 100 nm.

Use of SSNs

As described above, panels or kits of SSNs can be made in which each population of SSN in the panel has a unique SERS spectrum. Although the SERS activity of each population of SSNs in the panel is unique, the other properties of the SSNs—size, shape, composition of the outer layers, etc.—can be kept uniform across the panel. In embodiments in which SSNs are encapsulated, thereby sequestering the analyte from solvent, individual populations do not have different solvent or storage requirements. Also, each encapsulated SSN has the same exterior shell, simplifying the choice of chemistry either for attachment of molecules to the SSNs or attachment of the SNNs to solid supports.

The SSNs provided by the present invention can be used in virtually any assay in which a detectable tag or label is required. In one example, SSNs are used in biological and chemical assays as replacements for standard fluorescent tags. Indeed, SSNs possess a number of characteristics that make them far superior to prior art optical tags based on fluorophores. For example, assays using fluorophore detection are commonly hampered by the presence of autofluorescence and other background effects. In addition, many assays require use of a number of different fluorophores; different fluorophores commonly require different attachment chemistries and have different environmental requirements and sensitivities. Particularly noteworthy is the quenching of fluorescent activity that is observed when some fluorophores are conjugated to proteins. Finally, irreversible photodegradation resulting from the creation of a triplet or singlet excited state, followed by a non-reversible chemical reaction that permanently eliminates the excited state, places a severe limitation on the sensitivity of detection. By contrast, SSNs cannot be photobleached or photodegraded, have uniform chemical and physical properties, and can readily be resolved from the background. Perhaps most importantly, SSN detection is significantly more sensitive than fluorophore detection. Indeed, it is possible to tag a single molecule with a single SSN, and then detect the presence of that molecule using Raman spectroscopy. Such simple single molecule resolution is without parallel in the fluorophore detection art.

An example of a biological assay in which SSNs can be used as optical tags is the sandwich immunoassay. In sandwich assays, a target to be detected is captured by a solid surface. An antibody (or other ligand) to the same target is attached to a SSN, and then contacted with the solid support. Laser light of a suitable wavelength is then directed toward the solid surface, and the scattered light detected. The presence of the SSN SERS signal at the solid support indicates the presence of the antigen. In general, SSNs can be conjugated to any ligand that is used to detect the presence of a specific target in an assay.

In a specifically contemplated embodiment, SSNs are conjugated to nucleic acid molecules. In this way, they can be used in virtually any assay known in the art that detects specific nucleic acid sequences using optically-tagged nucleic acid probes.

SSNs are especially suitable for multiplexed chemical assays in which the identity of SSNs encodes the identity of the target of the assay. Prior art multiplexed assays that use fluorophores to encode target identity are subject to a number of severe constraints imposed by the physical and chemical properties of the fluorophores. Specifically, different fluorophores have different excitation maxima, so coincident excitation of multiple fluorescent tags is not possible. Moreover, fluorescence emission occurs in broad spectral bands, so the bands from one fluorophore often overlap with those of another. As a result, resolving even three different fluorescence activities requires sophisticated optics to separate and then detect the individual emission wavelengths. Because of these problems, multiplexed assays that use fluorophores rely on positional information to reveal target identity. Often, multiplexed assays with fluorophores use a solid support on which ligands are arranged in defined positions. The location of fluorophore signal reveals the identity of the target; the size of the fluorophore signal at that location indicates the amount of the target. However, the synthesis of solid supports with reagents localized at specific positions is expensive and time-consuming. There are limits on the number of features that may be defined on a single surface.

By contrast, the SSNs of the present invention offer remarkable spectral diversity and resolvability. As a result, SSNs can be used in multiplexed assays to yield quantitative and qualitative information without requiring the position-specific localization of reagents. Each SSN coupled to a target-specific reagent can encode the identity of that specific target, and the intensity of a particular Raman signal reveals the quantity of that target. For example, in the sandwich immunoassays described above, the identity of targets captured on the solid support can be determined by using a different flavor of SSN for each target.

Although SSNs are perfectly suited for use in multiplexing applications, they need not be used to encode identity in this manner. They can be used simply as replacements for fluorophores in multiplexed assays in which reagents are localized to specific positions on solid supports. When used in this way, the SSNs offer vastly more sensitive target detection than fluorophores.

Flow cytometry is an example of a multiplexed assay format in which the diversity and resolvability of SSNs can be fully exploited. In one such embodiment, populations of beads are provided to which primary antibodies against the targets to be detected are conjugated. The beads are contacted with the assay solution containing the targets, and also with a second set of antibodies against the targets. Each secondary antibody is conjugated to a SSN that encodes the identity of the target to which it will bind. The beads are then passed through a flow cytometer that acquires the Raman spectrum of each bead, thereby detecting the binding of the target to the bead and secondary antibody. Because the Raman spectrometer can sample all frequency space of each bead, it is even possible to place many different primary antibodies on a single bead; the Raman spectrum of each bead can be decoded to determine which SSNs are present and in what quantity; this in turn reveals how much of each target is bound to a single bead. It will be understood that there are many variations of this basic scheme, including the use of reagents other than antibodies to bind to the targets of interest. Accordingly, SSNs can be used in a multitude of variations on this scheme in which it is necessary or useful to tag a reagent.

The SSNs can also be used as optical tags for Microvolume Laser Scanning Cytometry (MLSC), rather than flow cytometry. MLSC is described in U.S. patent application Ser. No. 09/378,259, "Novel Optical Architectures for Microvolume Laser-Scanning Cytometers," filed Aug. 20, 1999, and U.S. patent application Ser. No. 09/558,094, "System for Microvolume Laser Scanning Cytometry," filed Apr. 26, 2000, both incorporated herein by reference in their entirety. In one embodiment of this system, a Raman microscope scans a capillary containing the reagents described above for the flow cytometry applications. The Raman microscope measures the Raman spectrum of each bead in the capillary, thereby obtaining quantitative data for each target to be detected. Again, it is the Raman signal of each SSN that encodes target identity; position specific reagents are not required.

In other embodiments, SSNs are used as optical tags in the solid support-based combinatorial chemical ("combi-chem") synthesis of libraries of novel compounds. One such method is known as "split and pool" synthesis. In this method, a preparation of suitably derivatized resinous beads is randomly divided into multiple populations, and each population is introduced into a different reaction mixture. Different reaction mixtures can contain different reagents, or the same reagents but different reaction conditions. Following reaction, the beads are then washed, recombined and divided again into a set of reaction mixtures. Because of the random manner in which the beads are distributed, each bead experiences a unique reaction history. The result is a bead-based library containing all of the compounds synthesized using the different permutations of the reaction mixtures. The library may then be screened to identify lead compounds with the desired activity. The lead compounds, in turn, can be analyzed to determine their composition and structure. The combi-chem method has been used to synthesize libraries of peptides, benzodiazapenes, and so on.

If the reaction history of an individual bead is known, then the chemical composition and structure of the compound attached thereto can be determined. There are several ways known in the art for encoding beads with their reaction history. In some methods, each reaction mixture contains a unique identifier molecule that becomes attached to the bead during the reaction step. At the completion of the synthesis, the identifier molecules can be cleaved from the bead of interest, and the reaction history of the bead can be determined by detecting the individual identifier molecules liberated from the bead. For example, prior art methods have used short oligonucleotides to encode reaction histories. These oligomers must be cleaved from the beads, amplified, and then sequenced in order to decode the reaction history; this is a time-consuming process. Because such identifier molecules must first be cleaved from the bead, it is necessary to choose a chemistry in which (a) cleaving the identifier from the bead does not modify or cleave the lead compound from the bead; and/or (b) cleaving the lead compound from the bead does not modify or cleave the identifier molecule. Moreover, the chemistry used to couple the identifier, and often just the presence of the identifier molecules themselves on the surface of the beads, may interfere with the actual combi-chem reactions. Such considerations place considerable restraints on all aspects of the chemistry used in encoded combi-chem synthesis.

The SSNs provided by the present invention can be used to encode the reaction history of beads in such combinatorial schemes. Each reaction mixture can contain a unique species of SSNs, such that each reaction step is accompanied by the attachment of a number of SSNs to the bead upon which the combinatorial synthesis takes place. For example, reaction mixture A can be encoded by $SSN^1$ when used at step 1 in the synthesis scheme, and by $SSN^2$ when used at step 2 in the synthesis scheme, and so on up to $SSN^n$ when used at step n in the synthesis scheme. At the end of the synthesis scheme, the individual beads may be screened for the desired lead compound activity. Beads with the desired lead compound activity are then examined by Raman spectroscopy. The Raman spectrum of each bead is then automatically decoded to detect the individual species of SSNs that have bound to each bead. This information reveals the reaction history of the bead, and hence the structure of the lead compound.

The use of SSNs to encode combi-chem synthesis schemes is a significant advance over the prior art. The entire reaction history of one bead can be determined by taking a single spectral measurement, without requiring that the bead undergo any physical or chemical manipulations. Indeed, the Raman spectrum can even be obtained in microtiter wells. Because the Raman activity of the SSNs can be measured without cleaving them from the bead, the constraints on the choice of chemistries outlined above are greatly reduced. Similarly, the only chemical groupings that the SSNs expose on the surface of the beads are the derivatizing groups that attach the SSN to the bead, and the stable encapsulant. Again, this greatly reduces the problems of identifier molecule interference with the combi-chem synthesis. Finally, the unprecedented spectral diversity offered by the SSNs enables the robust encoding of combi-chem schemes that are far more complex than allowed by prior art encoding methods.

Although SERS provides ample spectral diversity to allow many hundreds of differentiable SSNs to be made, in some applications it may be desirable to base the detection of an SSN on a combination of identifiable characteristics. In embodiments in which SSNs are formed as Nanobarcodes particles, it is particularly easy to add such additional identifying characteristics to the SSNs. For example, Nanobarcodes particles SSNs can have a unique optical signature based upon a combination of SERS activity (and/or one of the variants outlined above, e.g., SERRS, SEHRS, etc.) and a measurement of optical reflectivity, wherein the optical reflectivity measurement depends on the size, composition, and shape of the segments of the nanobar code.

In additional to biological applications, the SSNs of the present invention can be employed in a wide range of non-biological applications as tags or labels for a variety of objects, including but not limited to chemicals, molecules, materials, particles, paints, fasteners, tires, paper, documents, money, weapons, oil, or pills. When used as a tag, the SSN can be associated in any suitable way with the material that it labels. In these applications, it may be desirable to have tens of thousands or even millions of different codes; for example, handgun tracking applications require a unique code to be associated with each specific gun. The number of different potential codes can be increased by associating more than one SSN to the object of interest. For example, SSNs containing five different Raman-active analytes can be prepared, with analyte amounts varied by five factors of ten, to produce 50 distinguishable particle types. Ten-fold differences in analyte amount yield detectable differences in spectral intensity. Any number of the prepared particles can be added to each object to be tagged; for example, adding four such particles to each object provides for multi-particle combinations having over 105 different codes.

Manufacture of SSNs

Rod-shaped SSNs with carefully controlled lengths and diameters can be formed using the techniques described above for manufacturing Nanobarcodes particles. In these methods, metal layers are deposited into porous membranes by sequential electrochemical reduction of metal ions in solution. The sandwich structure is formed one stripe at a time within the pores of the membrane. Segments can instead be added using, for example, chemical vapor deposition or chemical self assembly. In addition to simple three-layer sandwich structures, particles with multiple SERS-active layers and multiple Raman-active analyte layers can be formed by this method. The porous membrane templates can be commercially available alumina or polycarbonate membranes, or they can be made by photolithographic methods. The particles themselves can also be manufactured by photolithographic methods.

A variety of additional methods can be used to make the intermediate Raman-active layer. In some embodiments, the intermediate layer is a metal oxide formed by oxidizing a previously deposited metal layer. For example, a rod with a structure of Au/Ni/Au can be oxidized to generate an intermediate layer of $NiO/Ni(OH)_2$ between two gold regions. Alternatively, a metal oxide can be electroplated directly onto one of the outer layers, followed by deposition of the final outer layer. For example, copper oxides can be electroplated from copper sulfate and lactic acid solutions, as described in J. A. Switzer et al., "Electrochemical Self-Assembly of Copper/Cuprous Oxide Layered Nanostructures," *J. Am. Chem. Soc.* 1998, 120, 3530-3531.

A polymer intermediate layer can be formed by growing a multi-layer polymer film on top of a first outer metal layer primed with a suitable material. The membrane is immersed in a polymer stock solution until a sufficiently thick layer is formed on the primer, which encourages growth of the layer and improves adhesion of the layer to the metal surface. For information on growing polymer layers, see N. I. Kovtyukhova et al., "Layer-by-Layer Assembly of Rectifying Junctions in and on Metal Nanowires," *J. Phys. Chem. B* 2001, 105, 8762-8769.

In an alternative embodiment, the intermediate layer is formed not as a homogeneous region of Raman-active analyte, but as a layer of analyte-coated SERS-active colloidal particles. For example, 10-nm diameter colloidal gold particles coated with the analyte can be added as a layer above the first SERS-active region, and then the second SERS-active region can be deposited above the colloid layer. In this case, the sandwich geometry is found both between the gold colloids in the intermediate layer and between the gold colloids and SERS-active outer layers.

After the particle is formed, it can be encapsulated in an encapsulant such as glass. To encapsulate in glass, the SSN is preferably treated first with a glass primer (that is, a material that can lead to growth of a uniform coating of glass, or can improve adhesion of the glass coat to the particle, or both). Glass is then grown over the metal nanoparticle by standard techniques well known in the art. Glass encapsulation methods are described in the following references, all of which are herein incorporated by reference: S. R. Hall et al., "Cocondensation of Organosilica Hybrid Shells on Nanoparticle Templates: A Direct Synthetic Route to Functionalized Core-Shell Colloids," *Langmuir* 2000, 16, 1454-1456; L. M. Liz-Marzán et al., "Synthesis of Nanosized Gold-Silica Core-Shell Particles," *Langmuir* 1996, 12, 4329-4335; and T. Ung et al., "Controlled Method for Silica Coating of Silver Colloids. Influence of Coating on the Rate of Chemical Reactions," *Langmuir* 1998, 14, 3740-3748.

It should be noted that the foregoing description is only illustrative of the invention. Various alternatives and modifications can be devised by those skilled in the art without departing from the invention. Accordingly, the present invention is intended to embrace all such alternatives, modifications and variances which fall within the scope of the disclosed invention.

What is claimed is:

1. A method of tagging a material, comprising associating with said material a particle of sandwich-type geometry comprising:
   at least two surface-enhanced spectroscopy (SES)-active outer layers comprising a metallic substance; an intermediate region comprising one or more spectroscopy-active molecule(s) positioned between said outer regions layers; and
   an encapsulant at least partially surrounding said outer layers and said spectroscopy-active molecule(s),
   wherein the particle has a maximum length of at most 300 nm, and wherein said particle has a measurable SES spectrum, and
   wherein the encapsulant does not interfere with the SES spectroscopy.

2. The method of claim 1, wherein said outer layers comprise Au, Ag, Cu, Na, Al, Li or Cr, wherein each other layer may comprise the same or different metal from the other outer layer or layers.

3. The method of claim 2, wherein said outer layers comprise Au.

4. The method of claim 2, wherein said outer layers comprise Ag.

5. The method of claim 2, wherein at least one of said outer layers comprises an alloy of metals comprising at least one metal chosen from Au, Ag, Cu, Na, Al, Li and Cr, wherein each outer layer may comprise the same or different metal or alloy of metals from the other outer layer or layers.

6. The method of claim 1, wherein said outer layers have a diameter less than about 200 nm.

7. The method of claim 6, wherein said outer layers have a diameter less than about 150 nm.

8. The method of claim 7, wherein said outer layers have a diameter less about 100 nm.

9. The method of claim 1, wherein said encapsulant has a thickness less than about 1 micron.

10. The method of claim 9, wherein said encapsulant has a thickness between about 0.5 nm and about 100 nm.

11. The method of claim 1, wherein said one or more spectroscopy-active molecule(s) forms a submonolayer coating on said outer layers.

12. The method of claim 1, wherein said one or more spectroscopy-active analyte molecule(s) forms a monolayer coating on said outer layers.

13. The method of claim 1, wherein said one or more spectroscopy-active analyte molecule(s) forms a multilayer coating on said outer layers.

14. The method of claim 1, wherein said encapsulant comprises a material chosen from glass, a polymer, a metal, a metal oxide, and a metal sulfide.

15. The method of claim 1, wherein said encapsulant comprises at least two materials chosen from glass, polymers, metals, metal oxides, and metal sulfides.

16. The method of claim 1, wherein said encapsulant comprises glass oxide ($SiO_x$).

17. The method of claim 1, wherein said encapsulant comprises $SiO_x$.

18. The method of claim 1, wherein said SES spectrum is obtained by a method chosen from SERS, SERRS, SEHRRS, and SEIRA.

19. The method of claim 1, wherein said one or more spectroscopy-active molecule(s) comprises an aromatic molecule.

20. The method of claim 1, wherein said material comprises a liquid.

21. The method of claim 20, wherein said material is selected from the group consisting of paper and oil.

22. The method of claim 1, wherein said material is selected from the group consisting of paper, documents, and money.

23. The method of claim 1 further comprising acquiring a SERS spectrum from said material.

24. The method of claim 1, wherein said encapsulant surrounds said layers and said spectroscopy-active molecule(s).

* * * * *